(12) United States Patent
Schoot

(10) Patent No.: US 8,157,745 B2
(45) Date of Patent: Apr. 17, 2012

(54) DEVICE AND METHOD FOR EXAMINATION OF A BODY CAVITY

(76) Inventor: Benedictus Christiaan Schoot, Eindhoven (NL)

( * ) Notice: Subject to any disclaimer, the term of this patent is extended or adjusted under 35 U.S.C. 154(b) by 20 days.

(21) Appl. No.: 11/792,440

(22) PCT Filed: Dec. 6, 2005

(86) PCT No.: PCT/NL2005/000838
§ 371 (c)(1),
(2), (4) Date: Mar. 7, 2008

(87) PCT Pub. No.: WO2006/062395
PCT Pub. Date: Jun. 15, 2006

(65) Prior Publication Data
US 2008/0275363 A1    Nov. 6, 2008

(30) Foreign Application Priority Data
Dec. 7, 2004   (NL) ...................................... 1027678

(51) Int. Cl.
*A61B 10/00* (2006.01)
(52) U.S. Cl. ........................................ 600/563; 600/562
(58) Field of Classification Search .................. 600/587, 600/591, 563, 562
See application file for complete search history.

(56) References Cited

U.S. PATENT DOCUMENTS

| 3,385,300 | A | * | 5/1968 | Holter | 604/275 |
| 3,438,366 | A | * | 4/1969 | Smith et al. | 600/570 |
| 3,542,031 | A | * | 11/1970 | Taylor | 604/118 |
| 3,636,940 | A | * | 1/1972 | Gravlee | 600/563 |
| 3,721,229 | A | | 3/1973 | Panzer | |
| 4,194,513 | A | * | 3/1980 | Rhine et al. | 600/563 |
| 4,445,517 | A | | 5/1984 | Feild | |
| 4,485,824 | A | | 12/1984 | Koll | |
| 4,534,362 | A | * | 8/1985 | Schumacher et al. | 600/551 |
| 4,709,705 | A | * | 12/1987 | Truglio | 600/563 |
| 5,540,658 | A | | 7/1996 | Evans et al. | |
| 6,451,012 | B2 | * | 9/2002 | Dobak, III | 606/24 |
| 6,485,410 | B1 | | 11/2002 | Loy | |
| 6,669,643 | B1 | * | 12/2003 | Dubinsky | 600/459 |
| 2002/0029006 | A1 | | 3/2002 | Turturro et al. | |
| 2007/0106174 | A1 | * | 5/2007 | Sanders et al. | 600/563 |

FOREIGN PATENT DOCUMENTS

| EP | 0 630 658 | 12/1994 |
| WO | WO 99/52441 | 10/1999 |

OTHER PUBLICATIONS

PCT/NL2005/000838, International Search Report and International Preliminary Report on Patentability, 10 pages, dated Feb. 10, 2006.

* cited by examiner

*Primary Examiner* — Max Hindenburg
*Assistant Examiner* — H. Q. Nguyen
(74) *Attorney, Agent, or Firm* — Wood, Phillips, Katz, Clark & Mortimer

(57) ABSTRACT

The invention relates to a device for carrying out an examination of a wall of a body cavity, in particular a uterus, which device comprises a catheter, supply means for supplying a sterile fluid to the body cavity via an outflow opening of the catheter, a sealing element for sealing the body cavity against leakage of the sterile fluid from the body cavity. The device furthermore comprises gripping means, operating means for operating the gripping means from a position outside the body cavity and transmission means for transmitting operating actions performed at the operating means to the gripping means, said transmission means extending through a further catheter via the sealing element, wherein said further catheter forms the catheter. The invention further relates to a method for examining a body cavity, using such a device.

14 Claims, 4 Drawing Sheets

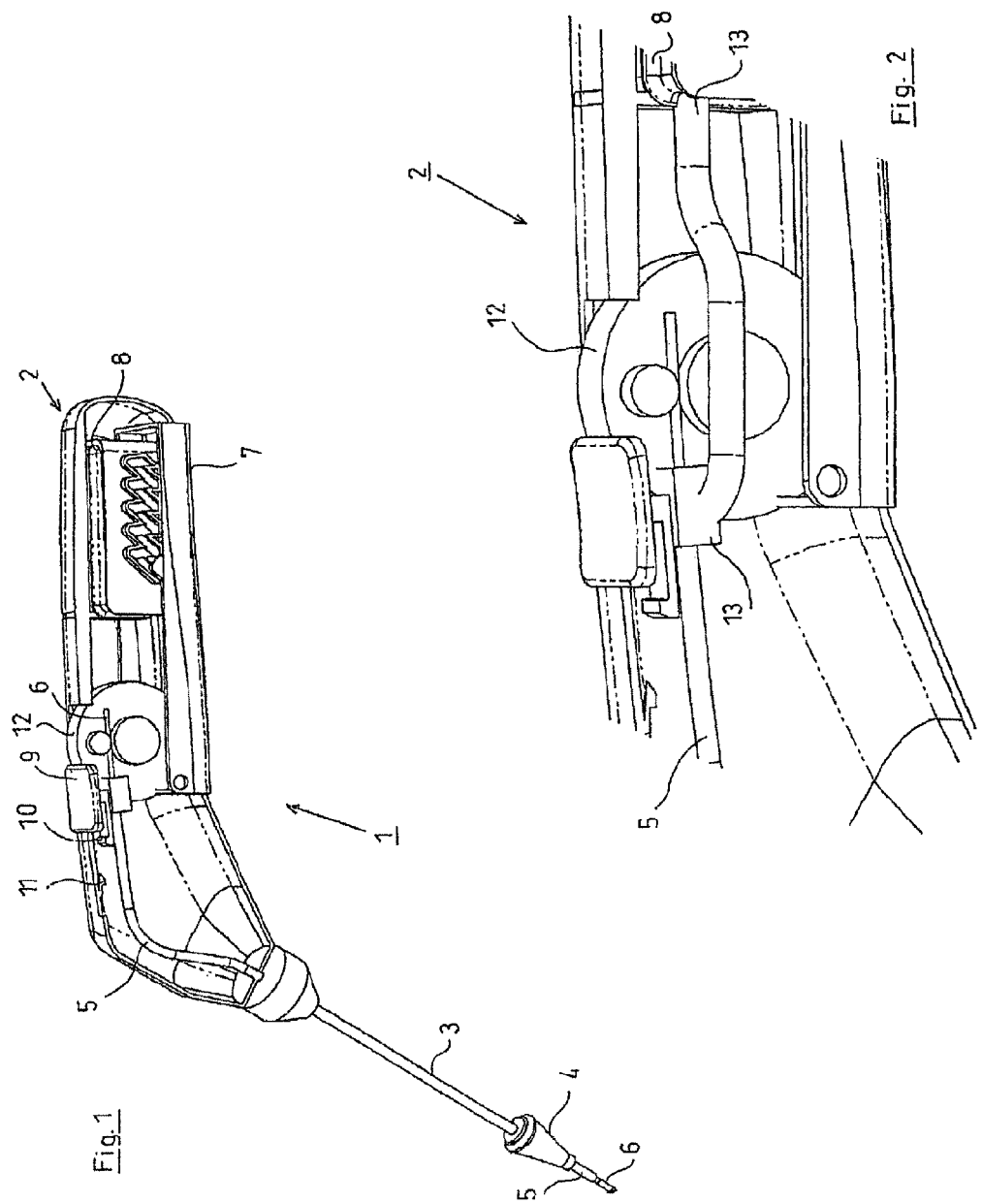

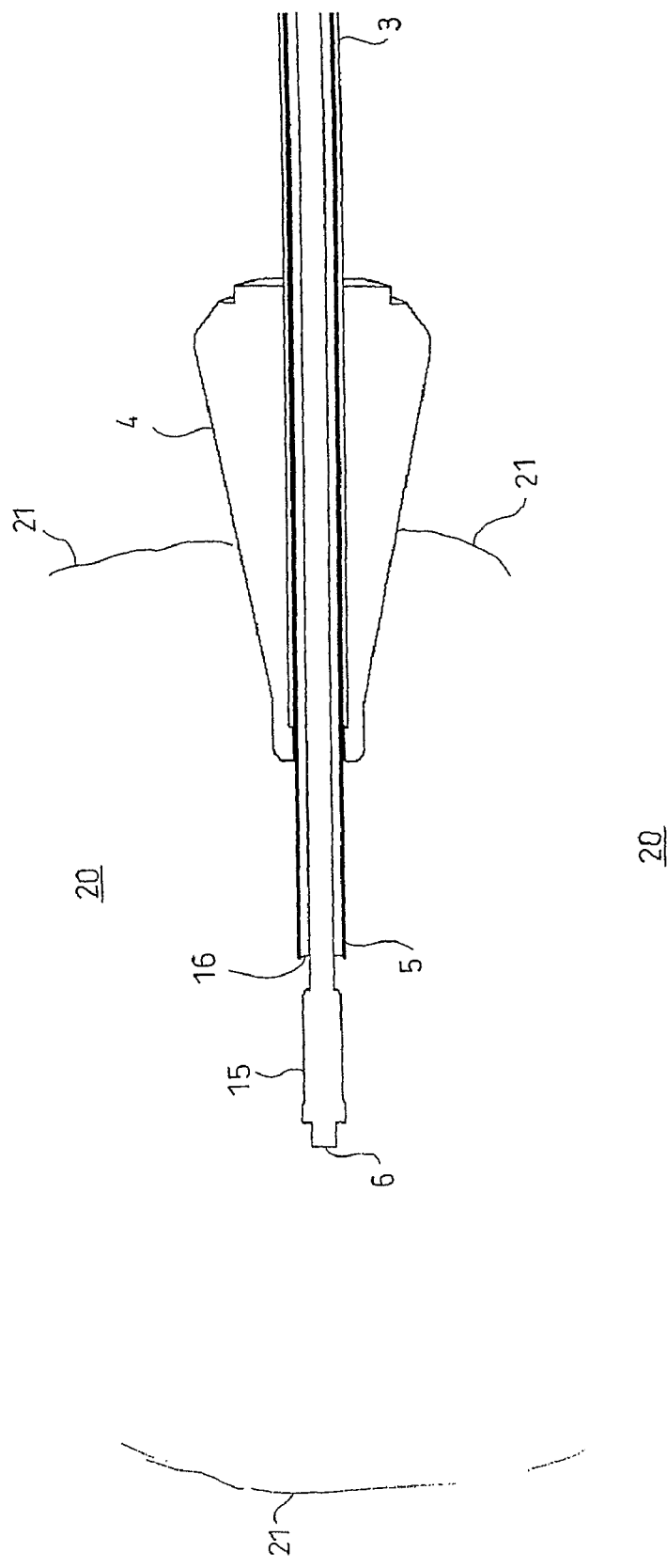

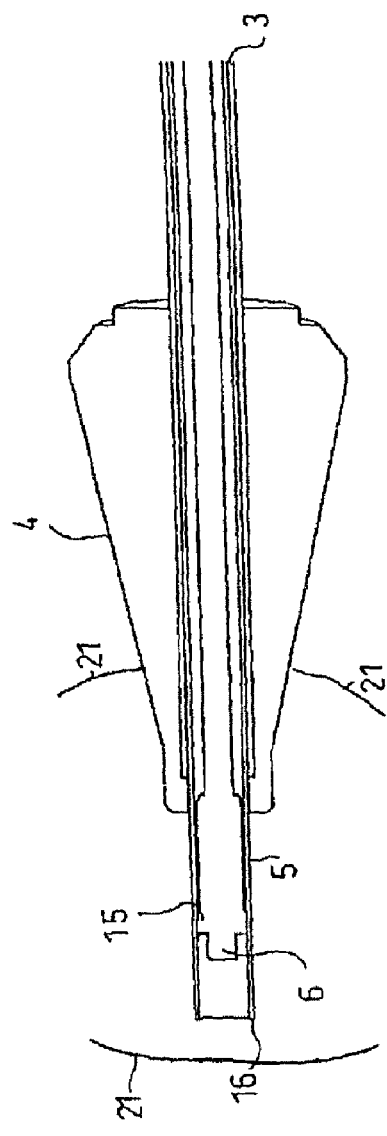
Fig. 4
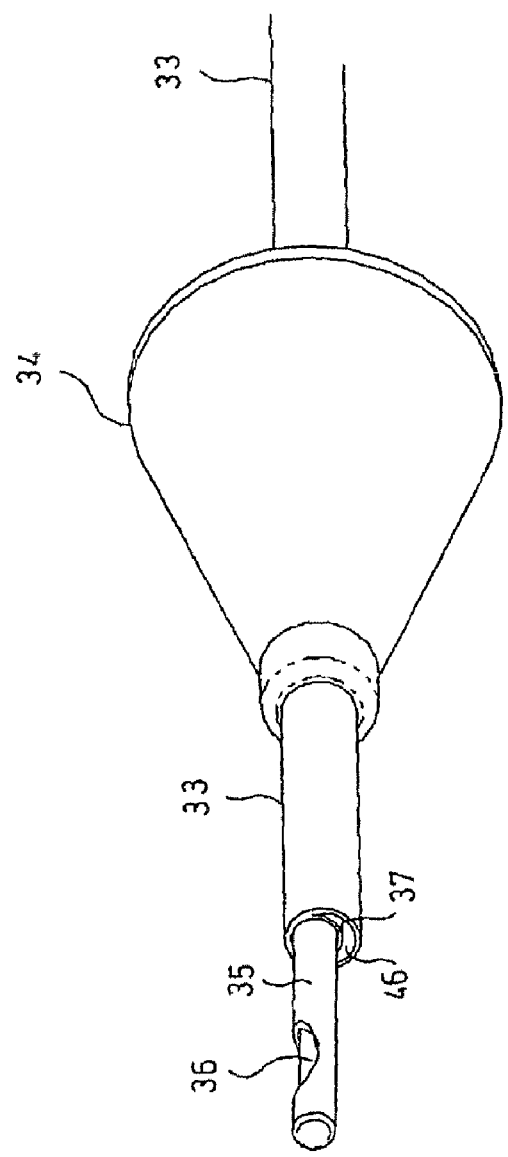
Fig. 5 - PRIOR ART

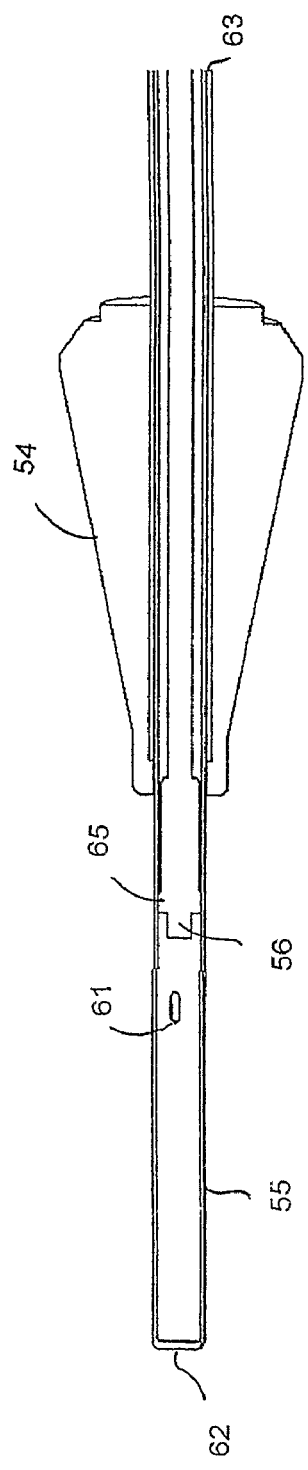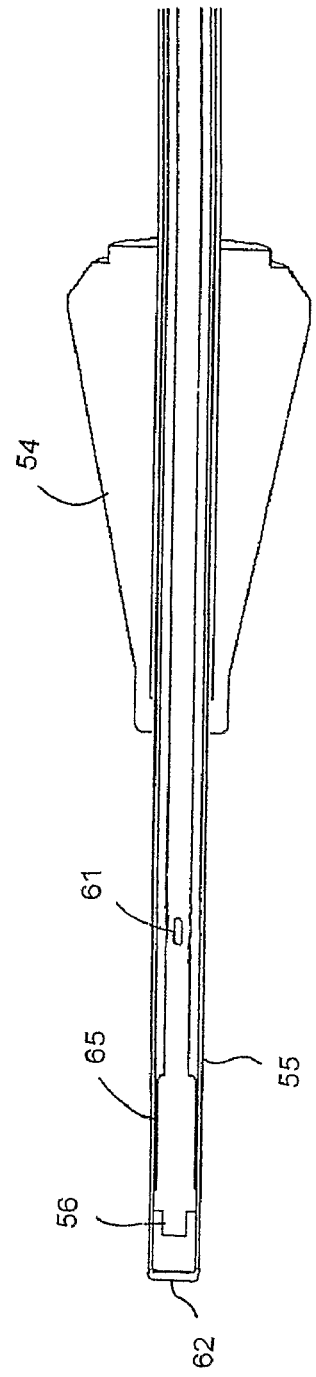
Fig. 6
Fig. 7

DEVICE AND METHOD FOR EXAMINATION OF A BODY CAVITY

BACKGROUND OF THE INVENTION

1. Field of the Invention

The present invention relates to a device for carrying out an examination of a wall of a body cavity, in particular a uterus, which device comprises a catheter, supply means for supplying a sterile fluid to the body cavity via an outflow opening of the catheter, a sealing element for sealing the body cavity against leakage of the sterile fluid from the body cavity, gripping means, operating means for operating the gripping means from a position outside the body cavity and transmission means for transmitting operating actions performed at the operating means to the gripping means, said transmission means extending through a further catheter via the sealing element.

2. Description of Related Art

Such a device is known from WO 99/52441, which discloses an apparatus for examination, excision and biopsy in a human body. The apparatus comprises a substantially tubular catheter and a biopsy device. The interior of the catheter accommodates a biopsy device comprising an associated biopsy catheter, being suitable for the passage of an intraluminal fluid through the catheter, which fluid can flow in via a fluid infusion opening. The catheter is substantially liquid-tight, except at the end thereof, so that fluid can flow through the catheter into the cavity to be examined via the end of the catheter. The biopsy device comprising the biopsy catheter is disposed in the interior of the catheter, being prevented from movement in radial or lateral direction within the catheter by the end of the catheter. Aspiration of tissue from the body cavity into the biopsy catheter is possible by operating a plunger and a piston extending within the biopsy catheter, which is surrounded by the catheter. The fluid can be supplied to the body cavity between the inner wall of the catheter and the outer wall of the further catheter.

A drawback of such a device, however, is the fact that the device is of complex construction. Consequently it is an object of the present invention to provide a device according to the preamble of claim 1, albeit a device of less complex construction. According to the present invention, this object is achieved in that said further catheter forms the catheter. Because of this aspect, a separate biopsy catheter is not needed, as the sterile fluid can be supplied to the body cavity via the biopsy catheter, so that a device of less complex construction than the known device can be used.

Furthermore, devices for introducing a fluid into a body cavity that is in communication with the environment, such as a uterus, are well-known in the medical world. In gynaecology, for example, hydro-sonography or "saline infused sonography" is a widely known examination method, wherein, in order to enable said sonography, a sterile fluid is injected into the uterus through a catheter for the purpose of stretching the wall of the uterus and obtaining a good sonographic contrast. This makes it possible to display deviations in shapes within the uterus. Said sonography may show that it is desirable to examine uteral wall tissue. This means that a follow-up examination is necessary, in which tissue is removed from the uteral wall, for example by aspirating tissue, which may be done by means of a microcurette. If the physician who carried out the sonography wants to carry out the follow-up examination directly thereafter, other instruments need to be introduced into the uterus through the vagina. This requires a great deal of dexterity on the part of the physician, however. In order to be able to carry out the two examinations in succession in an acceptable manner, at least two persons are required for successively removing and inserting the instruments. In addition, the examination is not very patient-friendly. That is why in many cases a new appointment is made for the follow-up examination in practice. Another drawback of the current method is that in many cases the physician does not decide whether a microcurettage is to be carried out until a transvaginal sonography has been carried out. This may lead to logistic problems, because the duration of the examination is uncertain because of this, so that the planning of appointments for the physician in question becomes unreliable. In addition, it is not clear in advance whether the presence of a second person for carrying out the examinations is necessary, so that also the further personnel planning becomes uncertain. In view of the existence of waiting lists, this is undesirable and possibly even irresponsible.

BRIEF SUMMARY OF THE INVENTION

The sealing element is preferably a cervix cone. A cervix cone has been designed especially for sealing the cervix against leakage of fluid from the uterus during the examination, thus rendering the device highly suitable for examination of the uterus.

In a preferred embodiment of the invention, the outflow opening is provided in a circumferential wall of the catheter. This causes the sterile fluid to flow laterally into the body cavity to be examined. In addition, the end of the catheter that is positioned in the body cavity in use can be configured as a closed end. This reduces the extent to which the catheter causes irritation with a person to be examined. A catheter provided with an outflow opening in its circumferential wall may also be used to the same advantage, independently of the present inventive concept, as a device for carrying out an examination of a wall of a body cavity, such as in particular a uterus, comprising a catheter and supply means for supplying a sterile fluid to the body cavity via an outflow opening of the catheter, characterized in that the outflow opening is provided in a circumferential wall of the catheter. Such a device might be combined with aspects of preferred embodiments as described in the present document.

Alternatively, the outflow opening is provided at an end of the catheter that is positioned in the body cavity in use. This embodiment is easier to manufacture, because the outflow opening is in fact formed by an open end of a tubular channel.

The catheter furthermore preferably comprises an aspiration opening, via which removed tissue can be introduced into the catheter. In this way tissue that is being/has been removed by the gripping means can be received in the catheter and be removed from the body cavity while present inside the catheter. The catheter wall protects the tissue against contamination during and after the removal thereof from the body cavity.

Preferably, the outflow opening and the aspiration opening coincide. In this way the outflow opening performs two different functions during the supply of sterile fluid and during the aforesaid removal, which renders the device less complex and less expensive.

Furthermore, the transmission means are preferably movable in longitudinal direction within the catheter. This makes it possible to insert the transmission means further into the uterus, if necessary, for example in order to manoeuvre the transmission means into position for removing tissue from the wall of the body cavity, whilst the sealing element is disposed on the catheter and needs to remain statically positioned during movement of the catheter so as to seal the uterus in a reliable manner.

Preferably, the gripping means comprises vacuum means for creating a vacuum at the aspiration opening in the catheter for removing tissue and/or moisture from the body cavity under said vacuum. The removal of tissue under a vacuum is a patient-friendly way of obtaining tissue to be examined, at least in a moist environment such as a uterus, in which a sterile fluid is present. The vacuum means may be a plunger, for example. By pulling the plunger through the catheter, away from the aspiration opening when the aspiration opening is positioned near tissue to be removed and the plunger is present between the aspiration opening and the operating means, a vacuum is created in the catheter at the location of the aspiration opening, as a result of which the tissue is sucked into the catheter. The plunger can be manually retracted, so that the physician who carries out the examination will have an adequate control over this so-called aspiration process. The process corresponds to the operation of a microsuction curette, an aspiration instrument that is well-known and frequently used in this field of the art. The very fact that generally known instruments are used will have a positive effect on the acceptance of the new device according to the invention by medical staff.

The gripping means in the catheter preferably forms a seal that functions to prevent sterile fluid present in the catheter from reaching the outflow opening in a sealing position. Thus, both the supply of sterile fluid to the body cavity and the aspiration of tissue through the aspiration opening in the catheter can be controlled by the gripping means. This leads to a simpler construction of the device and to a more convenient operation.

Preferably, the vacuum means is movable from a sealing position between the operating means and the outflow opening to a position beyond the outflow opening so as to release the outflow opening. In the sealing position, sterile fluid can be retained in the catheter, whilst said fluid can flow into the body cavity after the vacuum means has been moved to a position beyond the outflow opening. When the vacuum means is moved in opposite direction, it will create a vacuum in the catheter between the vacuum means and the aspiration opening once it has passed the aspiration opening.

The vacuum means is furthermore preferably provided with a thickened portion at the end thereof, which thickened portion can be moved to a position beyond the end of the catheter so as to release the outflow opening. This is a simple solution for rendering the catheter suitable both for inserting the sterile fluid and for removing tissue from the body cavity. The vacuum means only needs to engage the inner wall of the catheter along a small part of its length. The space between the non-thickened end of the plunger and the inner wall of the catheter can be used for supplying a sterile fluid to the thickened portion of the plunger or to the outflow opening if the thickened end is positioned beyond the outflow opening.

Furthermore preferably, the device comprises a holder in which the operating means are integrated and which is provided with connecting means which are suitable for detachably connecting the transmission means to the holder. For reasons of hygiene, a new or at least a sterile catheter must be used for every next patient, and the possibility of detachably connecting the transmission means to the holder makes it possible to use one holder for a number of examinations. This is attractive for economic reasons.

The operating means are furthermore preferably provided with locking means for locking the catheter against movement with respect to the holder. This makes it possible to lock the catheter in place once it is correctly positioned.

In another preferred embodiment according to the invention, the operating means are suitable for causing the vacuum means to move within the catheter in the locked position of the catheter. In this way a vacuum can be created in the catheter at the aspiration opening for removing tissue and/or moisture from the wall of the body cavity by pulling the vacuum means into the catheter, whilst the catheter is maintained in the desired position as a result of being locked in that position.

Furthermore preferably, the holder is provided with a reservoir for a sterile fluid. By containing the sterile fluid that is to be introduced into the body cavity in the holder, the things that are needed for the examination are provided in a very compact form.

The reservoir for sterile fluid is preferably detachable. Thus it is possible to provide a new reservoir containing a sterile fluid for every examination. This is required also for hygienic reasons.

In a preferred embodiment of the invention, the holder comprises pump means for pumping sterile fluid into the body cavity via the catheter. By providing the pump means at a suitable location of the holder, the pump means can be operated with the hand that holds the holder.

In a preferred embodiment, the pump means and the operating means are arranged for being operated with one hand when the holder is held with said one hand. By placing the pump means and the operating means on the holder in such a manner that they can be reached for being operated when the holder is being held, the physician will have one hand free at all times when carrying out the two examinations.

In a preferred embodiment, the catheter is connected to a vacuum pump for creating a vacuum at the aspiration opening in the catheter, which is positioned in the body cavity in use, so as to remove tissue from the body cavity. This is an alternative for a plunger that is manually operated.

In another preferred embodiment, the pump means comprise the vacuum pump and a device for reversing the action of the pump means. Thus it is possible to introduce sterile fluid into the body cavity and also to remove tissue from the wall of the body cavity by means of a vacuum while using only one pump.

The device is preferably at least partially made of a transparent material. In this way the physician who carries out the examination can see whether the operations he wishes to carry out or thinks he is carrying out by means of the device are actually being carried out in the desired manner.

The present invention further relates to a method for examining a body cavity, in particular a uterus, comprising the steps of introducing a sterile fluid into the body cavity by means of a catheter, for example for making an ultrasound scan, and removing tissue and/or moisture from the body cavity or the wall thereof, which steps are carried out by means of a device according to any one or more of the above described embodiments thereof. The advantages of this method correspond to the advantages as mentioned above with regard to the device according to the invention.

BRIEF DESCRIPTION OF THE DRAWINGS

The invention will be described in more detail hereinafter with reference to the following schematic figures, in which:

FIG. 1 shows an examination instrument according to the present invention, showing the holder in cutaway view;

FIG. 2 is a larger-scale view of a part of the examination instrument of FIG. 1;

FIG. 3 is a schematic view in longitudinal section of a part of the catheter of the examination instrument of FIG. 1;

FIG. 4 is a view of the catheter of FIG. 3, showing the outflow opening in the closed position thereof;

FIG. 5 shows a prior art device;

FIG. 6 is a schematic view in longitudinal section of an alternative embodiment of a part of the catheter of the examination instrument of FIG. 1, showing said part in a first condition thereof; and FIG. 7 is a schematic view in longitudinal section of the alternative embodiment of FIG. 6, showing said part in a second condition thereof.

DETAILED DESCRIPTION OF THE INVENTION

Referring to FIG. 1, an examination instrument 1 according to the invention is shown, which instrument comprises a holder 2, a non-flexible pipe 3 provided with a cervix cone 4, and a catheter 5, from which part of a plunger 6 projects at both ends. The holder 2 has a pivotable handle 7 and a reservoir 8 for introducing sterile fluid into the body cavity. The holder 2 is moreover provided with a slide knob 9 fitted with a hook 10 that can be hooked behind the latch 11. Present in the holder 2 is furthermore a rotary knob 12, to which one end of the plunger 6 is connected.

In FIG. 2, part of the interior of the holder of figure of 1 is shown on a larger scale, with the reservoir 8 being connected to the catheter 5 by means of a pipe 13.

FIG. 3 shows one end of the pipe 3 provided with the cervix cone 4, from which the catheter 5 projects outwardly. The cervix cone seals a uteral cavity 20 at the location of the uteral wall 21. In use the plunger 6 extends through the catheter 5 and projects outwardly from the catheter 5 at the outflow and aspiration opening 16, said plunger 6 being provided near its end with a widened portion 15 having an outer circumference that corresponds to the inner circumference of the catheter 5, which widened portion functions to seal the catheter.

FIG. 4 shows the same elements as FIG. 3, but in this case the plunger 6 occupies a slightly retracted position, as a result of which the outflow and aspiration opening 16 is closed by the widened portion 15 of the plunger 6.

FIG. 5 shows an alternative embodiment of a device that does not fall within the scope of the present patent application. This device has an outer catheter 33, being the catheter, through which a guide tube 37 and an inner catheter, being the further catheter, extends. In this case, too, a cervix cone 34 is provided on the outer catheter 33, and a plunger 36 is present in the inner, further catheter 35, which plunger can be distinguished in that part of the wall of the inner catheter 35 is cut away for the sake of clarity. In this embodiment, the outflow opening 46 for sterile fluid is present in a space between the outer wall of the inner, further catheter 35 and the inner wall of the outer catheter 33.

FIG. 6 shows an embodiment of one end of the pipe 63 provided with a cervix cone 54. A plunger 65 extends through a catheter 55, which plunger is retracted in the catheter 55 to a position near the cervix cone 54 in a sealing position. The catheter 55 is closed at the end 62. An outflow and aspiration opening 61 is provided between the plunger 65 and the end 62 of the catheter.

FIG. 7 shows the same embodiment as FIG. 6, in which the plunger 65 is positioned between the outflow and aspiration opening 61 and the end 62 of the catheter 55.

Referring to FIGS. 1-4, a description will now be given of the operation of the examination instrument 1 according to the present invention upon examination of the uteral wall (only partially indicated at 21), in which the pipe 3 into which the catheter 5 is retracted is inserted into the uteral cavity 20 via the vagina. Following that, the catheter 5 is moved past the end of the pipe 3 that is present in the uterus to a position in the uteral cavity 20 by means of the rotary knob 9, and finally the plunger 6 is moved even further inside the catheter 5 until the widened portion 15 extends beyond the outflow opening 16 of the catheter 5 (see FIG. 3). Then a sterile fluid from the reservoir 8 can be introduced into the uteral cavity 20 via the pipe 13 and the catheter 5 by means of the pivotable handle 7, with the cervix cone 4 being positioned in such a manner with respect to the cervix that it prevents the sterile fluid from flowing out of the uterus along the natural way. When sufficient fluid is present in the uteral cavity 20, an image is formed of the uteral wall by means of an ultrasound scan. Based on this image, the gynaecologist decides whether a sample of the uteral tissue needs to be taken. If that is the case, the catheter 5 is to that end locked in positioned with respect to the holder 2 by operating the slide knob 9, the hook 10 and the latch 11. Following that, the widened portion 15 of the plunger 6 can be retracted into the catheter 5 (FIG. 4) by rotating the rotary knob 12 clockwise. A vacuum is thereby created within the respective end of the catheter 5, as a result of which tissue from the uteral wall is collected in the respective end of the catheter 5, possibly together with fluid that is present in the uterus. Finally, the catheter 5 and the pipe 3 are removed from the uterus and the sample material can be stored for further examination in a sample reservoir intended for that purpose.

In FIG. 5 an alternative embodiment of a device that does not fall within the scope of the present patent application is shown by way of explanation. This device comprises an outer catheter 33 provided with a cervix cone 34, which outer catheter 33 comprises a tubular guide 37 whose external diameter is smaller than the internal diameter of the outer catheter 33. Extending within the tubular guide 37 is the inner, further catheter 35, within which a plunger 36 extends. Present between the tubular guide 37 and the inner wall of the outer catheter 33 is an outflow opening 46 for sterile fluid. In this embodiment the plunger 36 need not be provided with a widened portion at the end, because no sterile fluid needs to flow from the reservoir into the uterus in this case. After all, that takes place via the separate outflow opening 46. The construction of this device is more complex than that of the embodiments according to the invention that are shown in the other figures, because this device is provided with an extra guide 37 for the catheter. Moreover, this device will have to comprise means for verifying the supply of sterile fluid, which can be done by means of the plunger in the other embodiments as shown herein.

The principle of the operation of the embodiment of FIGS. 6 and 7 is not different from that of the embodiment that is shown in FIGS. 2 and 3. In this embodiment, too, the plunger 65 is moved from the position as shown in FIG. 6 between the outflow and aspiration opening 61 and the operating means (not shown) to the position as shown in FIG. 7 between the outflow and aspiration opening 61 and the end 62, so as to enable the supply of sterile fluid to the uterus (not shown) through the outflow and aspiration opening. Following that, the plunger 65 can be retracted into the catheter 55, with the plunger 65 creating a vacuum at the outflow and aspiration opening 66 when the plunger 65 is retracted further after having passed said outflow and aspiration opening 61.

Although the invention is shown in the figures without showing a hand that operates the examination instrument, it will be immediately apparent to those skilled in the art that an operator can hold the instrument in a manner that enables him or her to operate the pivotable handle 7 with his or her fingers and, whether or not simultaneously therewith, operate the slide knob 9 or the rotary knob 12 with his or her thumb. What is also important, however, is that it is no longer necessary to remove instruments from the uterus or insert other instruments into the uterus between the two successive examinations when an examination instrument such as the present one is used. Apart from the technical advantages as discussed in the foregoing, it will be readily understood that the use of such an examination instrument is significantly more patient-friendly than the existing examination methods, in which examination instruments need to be exchanged for other instruments between two examinations.

The embodiments as described herein only serve to illustrate and explain the invention. The embodiments are by no means intended to limit the scope of the invention as defined in the appended claims. Many variants are conceivable, which all fall within the scope of the invention. Thus it is possible, for example, to make the action of the pump reversible or to provide a different type of a gripper instead of the vacuum device for removing tissue.

The invention claimed is:

1. A device (1) for carrying out an examination of a uterus (20), comprising:
   a holder (2) having a tube (3) mounted thereon;
   a catheter (5) slidably disposed within said tube (3), and defining an outflow opening (16);
   a first operating knob (9), mounted on said holder, operatively connected to said catheter for slidably moving said catheter with respect to said tube (3);
   a supply of sterile fluid to be supplied to the uterus (20) via said outflow opening (16) of the catheter (5);
   a sealing element (4) mounted on said tube (3) to seal the uterus against leakage of the sterile fluid from said uterus,
   the catheter movable slidably with respect to the tube to thereby change a spacing between the sealing element and the outflow opening;
   a plunger (6) slidably disposed within said catheter, said plunger (6) having a widened portion (15); and
   a second operating knob (12), mounted on said holder (2), operatively connected to said plunger (6) for reciprocably moving said plunger relative to the catheter,
   said widened portion (15) of said plunger being positionable to be spaced distally of said outflow opening (16) to permit the sterile fluid to be supplied through the outflow opening to the uterus, said widened portion (15) of said plunger (6) being movable proximally of said outflow opening so that said plunger (6) functions with said catheter (5) to cause the widened portion moving proximally to create a vacuum at said outflow opening (16) to permit a tissue sample from within the uterus (20) to enter said outflow opening (16) for removal from the uterus (20).

2. A device according to claim 1, characterized in that the sealing element is a cervix cone.

3. A device according to claim 1, characterized in that the outflow opening is provided in a circumferential wall of the catheter.

4. A device according to claim 2, characterized in that the outflow opening is provided at an end of the catheter that is positioned in the uterus (20) in use.

5. A device according to claim 1, characterized in that the plunger in the catheter forms a seal that functions to prevent sterile fluid present in the catheter from reaching the outflow opening in a sealing position.

6. A device according to claim 3, characterized in that the plunger is movable from a sealing position proximally of the outflow opening to a position distally beyond the outflow opening so as to open the outflow opening.

7. A device according to claim 1, characterized in that the first operating knob (9) is provided with locking means for locking the catheter against movement with respect to the holder.

8. A device according to claim 7, characterized in that the second operating knob (12) is suitable for causing the plunger to move within the catheter in the locked position of the catheter.

9. A device according to claim 1, characterized in that the holder is provided with a reservoir for the supply of sterile fluid.

10. A device according to claim 9, characterized in that the reservoir for sterile fluid is detachable.

11. A device according to claim 1, characterized in that the holder comprises means for pumping sterile fluid into the uterus via the catheter.

12. A device according to claim 11, characterized in that the pump means and the first and second operating knobs are arranged for being operated with one hand when the holder is held with said one hand.

13. A device according to claim 1, characterized in that the device is at least partially made of a transparent material.

14. A method for examining a uterus, comprising the steps of introducing a sterile fluid into the body cavity by a catheter, for making an ultrasound scan, and removing tissue and/or moisture from the uterus or the wall thereof, characterized in that said steps are carried out by a device according to claim 1.

* * * * *